United States Patent [19]

Dorlars et al.

[11] 3,957,817
[45] May 18, 1976

[54] 3-ARYL-7-PYRAZOLYL-COUMARINS

[75] Inventors: Alfons Dorlars; Otto Neuner, both of Leverkusen, Germany

[73] Assignee: Bayer Aktiengesellschaft, Leverkusen, Germany

[22] Filed: Nov. 5, 1969

[21] Appl. No.: 874,409

[30] Foreign Application Priority Data
Nov. 5, 1968  Germany............................ 1806996

[52] U.S. Cl........................... 260/310 R; 252/301.27
[51] Int. Cl.²........................................ C07D 311/16
[58] Field of Search................................ 260/310 R

[56] References Cited
UNITED STATES PATENTS
3,123,617    3/1964    Hausermann.................... 260/310 R
FOREIGN PATENTS OR APPLICATIONS
1,223,312    2/1971    United Kingdom............. 260/310 R
6,802,036    8/1968    Netherlands..................... 260/310 R

*Primary Examiner*—Natalie Trousof
*Attorney, Agent, or Firm*—Plumley & Tyner

[57] ABSTRACT

3-Aryl-7-pyrazolyl-coumarin compounds of the formula

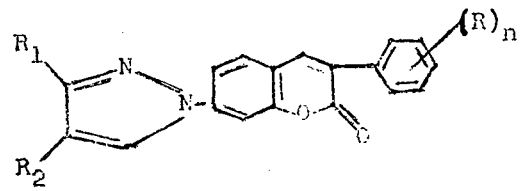

in which R stands for hydrogen, halogen, alkyl or alkoxy radicals, $n$ represents the numbers 1–3, $R_1$ and $R_2$ represent, hydrogen or alkyl or phenyl radical, $R_1$ and $R_2$ may also form, together with the two carbon atoms of the pyrazole ring, a non-aromatic carbocyclic, 5- or 6-membered ring system, radical as well as their production and use as brightening agents.

4 Claims, No Drawings

3-ARYL-7-PYRAZOLYL-COUMARINS

The subject matter of the present invention comprises new 3-aryl-7-pyrazolyl-coumarin compounds of the formula

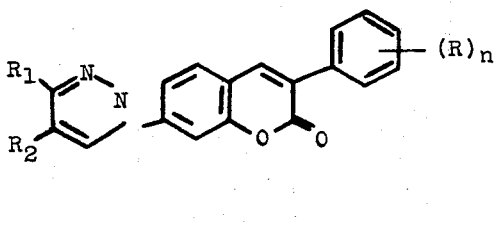

(I)

in which
R stands for hydrogen, halogen, alkyl or alkoxy radicals,
n represents the numbers 1–3, and
$R_1$ and $R_2$ represent, independently of one another, hydrogen or an optionally substituted alkyl or phenyl radical, $R_1$ and $R_2$ may also form, together with the two carbon atoms of the pyrazole ring, a non-aromatic carbocyclic, 5- or 6-membered ring system, with the proviso that either $R_1$ and $R_2$ form, together with the two carbon atoms of the pyrazole ring, a non-aromatic carbocyclic, 5- or 6-membered ring system or that at least one of the radicals $R_1$ or $R_2$ represent an optionally substituted phenylalkyl radial or an optionally substituted phenyl radical, as well as their production and use as brightening agents.

Preferred compounds of the formula (I) are those in which $R_1$ and $R_2$ represent optionally substituted phenylalkyl or phenyl radicals and also those in which $R_2$ stands for an optionally substituted phenyl radical, and $R_1$ denotes hydrogen or alkyl, as well as those in which $R_1$ represents an optionally substituted phenyl radical, and $R_2$ stands for hydrogen or for alkyl.

Suitable substituents R are halogen atoms, such as fluorine, bromine and, in particular, chlorine, furthermore alkyl radicals with preferably 1–4 carbon atoms, such as methyl, ethyl, iso- and tert.-butyl radicals as well as alkoxy groups with preferably 1–4 carbon atoms, such as methoxy, ethoxy and butoxy radicals.

Suitable alkyl radicals $R_1$ and $R_2$ are, for example, straight-chain, branched or cyclic alkyl radicals with up to 8 carbon atoms, which may be substituted by halogen atoms, especially fluorine, chlorine or bromine, hydroxyl groups, acyloxy groups, especially acetoxy, butyroxy and benzoyloxy groups, alkoxy groups, especially methoxy, ethoxy and butoxy groups, or by optionally substituted phenyl radicals, for example, phenyl, tolyl or chlorophenyl radicals.

Examples of radicals of this type are inter alia: methyl, benzyl, ethyl, β-hydroxyethyl, acetoxyethyl, β-chloroethyl, β-methoxyethyl, β-ethoxyethyl, β-phenethyl, propyl, butyl, isobutyl and tert.-butyl radicals.

The term optionally substituted phenyl radicals particularly comprises those phenyl radicals which can carry one or more of the following substituents; fluorine, chlorine, bromine, alkyl groups with 1–4 carbon atoms as well as alkoxy groups with 1–4 carbon atoms. The following may be mentioned by way of example: o-, m- and p-tolyl, o-, m- and p-chlorophenyl, o-, m- and p-anisyl radicals, p-bisphenyl radicals. However, unsubstituted phenyl radicals are preferred.

The non-aromatic carbocyclic ring system for which $R_1$ and $R_2$ may together stand, may contain fused aromatic rings. Examples of such radicals are the following:

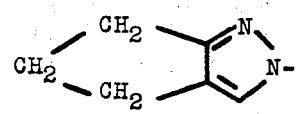

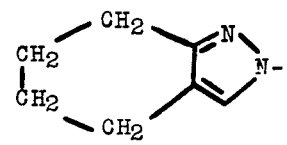

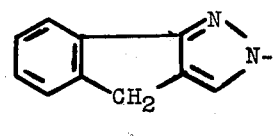

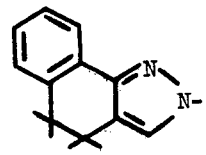

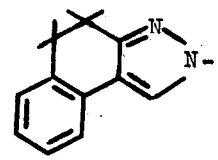

The pyrazolyl-coumarins of the formula (I) are new. They are colourless to greenish yellow crystalline compounds the virtually colourless solutions of which have an intense blue fluorescence in ultra-violet light and which are eminently suitable to be used as optical brightening agents for synthetic materials, especially for the brightening of materials of aromatic polyesters, polyvinyl chloride, polyacrylonitrile, polyamides, polyurethanes, polyalkenes and cellulose acetates. They can be used in conventional manner, e.g. in the form of aqueous dispersions or in the form of solutions in neutral solvents. In particular, fabrics containing polyester fibres or made from polyester fibres can be outstandingly brightened by padding with aqueous disperse preparations of compounds of the formula (I) and subsequent thermal after-treatment. They can also advantageously be incorporated into casting, moulding and spinning compositions which are used for the production of foils or filaments, in this case they may also be admixed with the monomers or pre-condensates which serve for the production of synthetic materials. The amounts of brightening agents required in each case can readily be established by preliminary experiments; in general, they range between 0.01 and 0.5%, referred to the weight of the substrate to be brightened.

The brightening effects obtained ae distinguished by outstanding fastness to light, thermal stability and resistance against bleaching agents in an acidic and neutral range. Compared with the nearest comparable pyrazolyl-coumarins described in U.S. Pat. No. 3,123,617, the present new compounds are characterised by better brightening effects in the technically important use as brighteners for polyester spinning compositions and as brighteners for polyester fabrics when used in the padding process according to the thermosol process.

Thus, for example, the 7-[3'-phenylpyrazolyl-(1')]-3-phenylcoumarin according to the invention has surprisingly better brightening effects than the 7-[3'-methylpyrazolyl-(1')]-3-phenylcoumarin disclosed in U.S. Pat. No. 3,123,617, Example 3; the 7-[3'- and 4'-phenylpyrazolyl-(1')]-3-phenylcoumarins according to the invention are also very substantially superior to the 7-[5'-phenylpyrazolyl-(1')]-3-phenylcoumarin described in Example 6 of the Patent mentioned above.

Examples of suitable pyrazolyl-coumarin compounds of the formula (I) are set out in the following Table:

Table

| | $R_1$ | $R_2$ | R |
|---|---|---|---|
| a | phenyl | H | H |
| b | 3-methylphenyl | H | H |
| c | 4-chlorophenyl | H | H |
| d | 3-methoxyphenyl | H | H |
| e | phenyl | $CH_3$ | H |
| f | phenyl | $C_2H_5$ | H |
| g | phenyl | $-CH(CH_3)_2$ | H |
| h | phenyl | $-CH_2-$phenyl | H |
| i | phenyl | $-CH_2-CH_2-$phenyl | H |

Table — Continued

| | R₁ | R₂ | R |
|---|---|---|---|
| k | biphenyl | H | H |
| l | H | phenyl | H |
| m | H | —C₆H₄—CH₃ | H |
| n | CH₃ | phenyl | H |
| o | CH₃ | —CH₂—phenyl | H |
| p | C₂H₅ | phenyl | H |
| q | cyclohexyl | phenyl | H |
| r | —CH₂—phenyl | phenyl | H |
| s | phenyl | phenyl | H |
| t | H | phenyl | p—CH₃ |
| u | H | phenyl | p—Cl |
| v | H | phenyl | p—OCH₃ |
| w | H | phenyl | m—Cl |
| x | H | phenyl | m—OCH₃ |
| y | H | phenyl | m—CH₃ |

Table — Continued

| | $R_1$ | $R_2$ | R |
|---|---|---|---|
| z | | $-(CH_2)_3-$ | H |
| $a_1$ | | $-(CH_2)_4-$ | H |
| $b_1$ | | 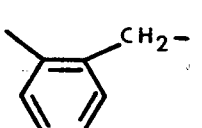 | H |
| $c_1$ | | 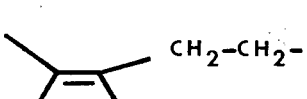 | H |
| $d_1$ | | 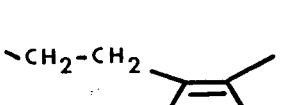 | H |

The new phenylpyrazolyl-coumarin compounds of the formula (I) can be produced by various methods.

The condensation of 7-hydrazinocoumarin compounds with γ-aryl-γ-ketoaldehydes or their functional derivatives, some of which are described in U.S. Pat. No. 3,123,617 (e.g. in Example 6) is not suitable since it leads preponderantly or even exclusively to 7-[5′-arylpyrazolyl-(1′)]-coumarins which are without value as brightening agents in comparison with the isomeric 7-[3′-arylpyrazolyl-(1′)]-coumarin compounds with a free 5′-position according to the invention.

The 7-pyrazolyl-coumarins of the formula (I) according to the invention which are unsubstituted in the 5-position of the pyrazole radical can be obtained by condensing hydrazino-coumarins of the formula

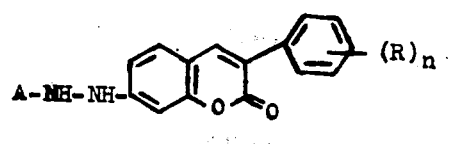 (II)

in which
  A represents an acyl radical or a sulphonic acid group;

R and n have the same meaning as given in formula (I), with vinyl ketones of the formula

 (III)

in which
  R and $R_2$ have the same meaning as given in formula (I), and
  Z stands for the hydroxyl group, for an alkoxy group, an acyloxy group, a dialkylamino group, or for a halogen atom,
while retaining the radical A, condensation products of the probable formulae

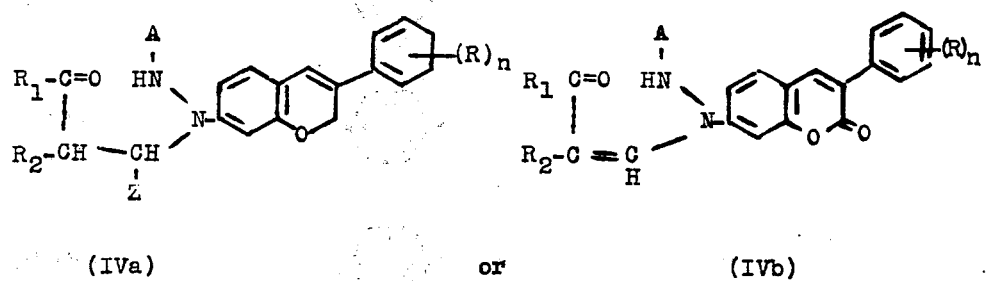

(IVa)    or    (IVb)

being formed, subsequently cyclizing the latter, optionally after an intermediary isolation, while eliminating A—OH.

The condensation of (II) with (III) is expediently carried out in a neutral to weakly acidic organic medium at temperatures of about 40°–100°C. The elimination of A—OH from the reaction products thus obtained takes place under the influence of strong acids, for example, mineral acids, such as hydrochloric acid, at temperatures of about 80°–120°C.

Pyrazolyl-coumarin compounds of the formula (I) in which $R_1$ stands for hydrogen, whilst $R_2$ and R have the above-mentioned meaning, can be produced in a simple manner by condensation of the free 7-hydrazinocoumarins (IIa), [A=H], or their salts, for example, the salts with mineral acids, such as hydrochloric acid, with malon(di)aldehydes of the formula (III) [$R_1$ = H; $R_2$ = an optionally substituted phenyl radical, Z = OH], or their functional derivatives, for example, enamines, anil, acetal or bisulphite compounds, for example, by heating to about 80°–110°C. in glacial acetic acid.

Acyl radicals are, for example, the formyl, acetyl, oxalyl and propionyl radical.

Examples of vinyl ketones of the formula (III) are, inter alia:

phenyl-β-hydroxyvinylketone, p-tolyl- and p-anisyl-β-hydroxyvinylketone, phenyl-β-methoxyvinylketone, phenyl-β-chlorovinylketone, o-, m- and p-chlorohenyl-β-chlorovinylketone, o-, m- and p-tolyl-β-chlorovinylketone, o-, m- and p-anisyl-β-chlorovinylketone, phenyl-(α-methyl-β-hydroxyvinyl)-ketone, phenyl-(α-ethyl-β-hydroxyvinyl)-ketone, phenyl-(α-propyl-β-hydroxyvinyl)-ketone, phenyl-(α-isopropyl-β-hydroxyvinyl)-ketone, phenyl-(α-benzyl-βhydroxyvinyl)-ketone, phenyl-(α-phenyl-β-hydroxyvinyl)-ketone, tolyl-(α-tolyl-β-hydroxyvinyl)-ketone, phenyl- and tolyl-malon(di)aldehyde, p-biphenyl-β-hydroxyvinylketone, α-phenyl- and α-tolyl-β-dimethylaminoacrolein, methyl-(α-phenyl -β-hydroxyvinyl)-ketone, methyl-(α-benzyl-β-hydroxyvinyl)-ketone, ethyl-(α-phenyl-β-hydroxyvinyl)-ketone, cyclohexyl-(β-phenyl-α-hydroxyvinyl)-ketone, benzyl-(α-phenyl-β-hydroxyvinyl)-ketone, 1,4-diphenyl-2-hydroxymethylene-butanone-(1), 2-hydroxymethylene-cyclopentanone-(1), 2-hydroxymethylene-cyclohexanone-(1), 2-hydroxymethylene-indanone-(1), 2-hydroxymethylene-tetralone-(1), 1-hydroxymethylene-tetralone-(2), as well as their methyl ethers.

Examples of hydrazinocoumarins of the formula (II) are the formyl, acetyl and propionyl derivatives of 3-phenyl-, 3-p-chlorophenyl, 3-p-methylphenyl-, 3p-methoxyphenyl-7-hydrazinocoumarin or the corresponding hydrazino-monosulphonic acids.

The pyrazolyl-coumarin compounds of the formula (I) can also be obtained by reacting N-[3-phenyl-coumarinyl-(7)]-sydnones of the formula (V) with alkines of the formula (VI)

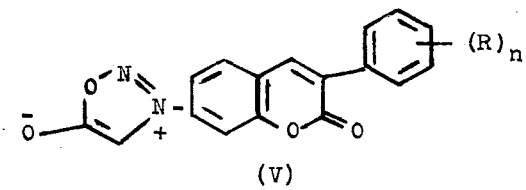

(V)

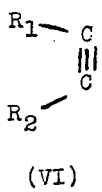

(VI)

in which,

R, $R_1$ and $R_2$ as well as n have the same meaning as above, for example, according to the process of U.S. Pat. No. 3,254,093. Those compounds of the formula (I) in which $R_2$ represents hydrogen, whilst $R_1$ stands for an optionally substituted phenyl radical and R has the meaning given above, can be obtained by reacting coumarinyl sydnones of the formula (V) with alkenes of the formula (VII)

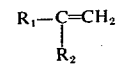

(VII)

according to the process of German Patent Specification No. 1,210,431, $R_1$ and $R_2$ having the same meaning as above. The sydnones of the formula (V) can be produced according to known processes by alkylation of 7-amino-3-arylcoumarins with haloacetic acids, nitrosation of the resultant coumarinyl-aminoacetic acids and cyclodehydration of the N-nitrosocoumarinyl-aminoacetic acids thus obtained. Suitable alkines and alkenes are, for example, the following: phenylacetylene, p-chlorophenyl-acetylene, p-methyl-phenylacetylene, tolan, 1-phenyl-2-methylacetylene and 1,1-diphenylethylene.

Another process for the production of pyrazolyl-coumarin compounds of the formula (I) consists in treating pyrazolinyl coumarins of the formula (VIII)

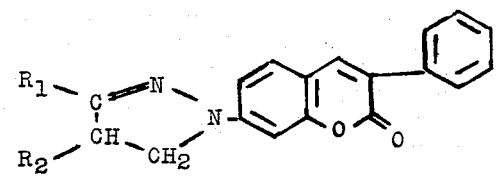

(VIII)

in which

R, $R_1$ and $R_2$ have the meaning given in formula (I), with dehydrating agents according to the process described in U.S. Pat. No. 3,123,612.

The degrees given in the Examples are degrees centigrade.

EXAMPLE 1

26 g 7-hydrazino-3-phenylcoumarin are stirred together with 19 g α-phenyl-β-dimethylaminoacrolain in 150 ml glacial acetic acid at 95°–100° for 30 minutes. The mixture is boiled under reflux for a further 30 minutes, the precipitated crystals are filtered off with suction after cooling, and purified by redissolving from dimethyl formamide. 20.6 g (78% of theory) 3-phenyl-7-[4'-phenylpyrazolyl-(1')]-coumarin (1a) are obtained in the form of pale, slightly yellowish leaflets of m.p. 272°–273° which, dissolved in dimethyl formamide, have an intense blue fluorescence.

In an analogous manner there are obtained the phenylpyrazolyl-coumarins set out in the Table below by reacting the 7-hydrazino-3-arylcoumarins indicated in each case with phenylmalon(di)aldehyde or α-phenyl-β-dimethylaminoacrolein.

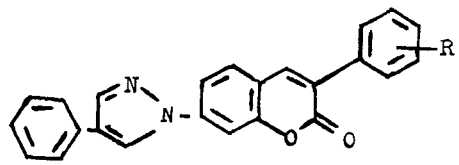

20 ml concentrated hydrochloric acid are then added, and the reaction mixture is stirred at 105°–110° for 1 hour. The mixture is subsequently cooled, the precipitated crystalline pyrazole derivative is filtered off with suction, washed with glacial acetic acid and methanol, and dried. 20 g of a beige-coloured powder are obtained which, for purification, is redissolved from chlorobenzene with the addition of bleaching earth (tonsil) and from dimethyl formamide. The 3-phenyl-7-[4-phenyl-3-methylpyrazolyl-(1′)]-coumarin of the formula (a) thus obtained in the pure form yields pale greenish yellow crystals of m.p. 190°–192°, which have an intense blue fluorescence in organic solvents.

The α-phenyl-acetoacetaldehyde used for the condensation was obtained by condensing phenylacetone with ethyl formate in the presence of sodium ethylate.

In an analogous manner there are obtained the phenylpyrazolyl coumarins set out in the Table below by acylation of 7-hydrazino-3-phenylcoumarin with acetanhydride or formic acid and reaction of the resultant acylhydrazinocoumarin compound with the vinyl ketone indicated for each case.

| Example 1 | R | m.p. | hydrazinocoumarin used |
|---|---|---|---|
| (a) | H | 272–273°C | 7-hydrazino-3-phenylcoumarin |
| (b) | p-CH₃ | 279–280°C | 7-hydrazino-3-p-tolylcoumarin |
| (c) | p-Cl | 300–301°C | 7-hydrazino-3-p-chlorophenyl-coumarin |
| (d) | m-Cl | 270–272°C | 7-hydrazino-3-m-chlorophenyl-coumarin |
| (e) | p-OCH₃ | 277–278°C | 7-hydrazino-3-p-anisylcoumarin |

EXAMPLE 2

26 g 7-hydrazino-2-phenylcoumarin are suspended in 250 ml glycol methyl ether; 11 g acetanhydride are added dropwise at room temperature, while stirring, the mixture being spontaneously heated to about 40°. The resultant clear solution of the acetylhydrazino-phenylcoumarin is mixed with 17 g α-phenylacetoacetaldehyde (=hydroxy-methylenebenzyl-methylketone and stirred at 50° for 3 hours. The bulk of the addition product of the hydroxy-methylene compound with the hydrazide precipitates in the form of yellow crystals which need not be isolated for further reaction. Heating is continued at 70° for another hour,

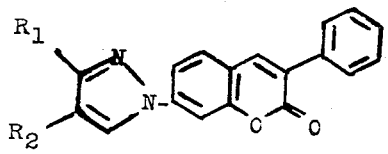

| | $R_1$ | $R_2$ | m.p. | vinyl ketone |
|---|---|---|---|---|
| a | CH₃ | phenyl | 190–192° | α-phenyl-acetoacetaldehyde |
| b | C₂H₅ | phenyl | 181–184° | hydroxymethylene-benzyl ethyl ketone |
| c | cyclohexyl | phenyl | 233–234° | hydroxymethylene-benzyl-cyclohexyl ketone |
| d | -CH₂-phenyl | phenyl | 193–194° | hydroxymethylene-benzyl-benzyl ketone |
| e | phenyl | phenyl | 258–259° | hydroxymethylene-desoxy-benzoin |
| f | phenyl | H | 205–206° | methoxymethylene-acetophenone or phenyl β-chlorovinyl-ketone |
| g | phenyl | CH₃ | 224–225° | hydroxymethylene-propiophenone |

| R₁ | R₂ | m.p. | -continued vinyl ketone |
|---|---|---|---|
| h  | i-C₃H₇ | 246–247.5° | hydroxymethylene-isovalero-phenone |
| i  | -CH₂- | 205–206.5° | phenyl-(α-benzyl-β-hydroxyvinyl)-ketone |
| k CH₃ | -CH₂- | 185–186.5° | methyl-(α-benzyl-β-hydroxyvinyl)-ketone |
| l —(CH₂)₄— | | 236–237.5° | 2-hydroxymethylene-cyclohexanone-(1) |
| m  | | | 2-hydroxy-methylene-indanone-(1) |
| n  | | 236–237° | 2-hydroxymethylene-tetralone-(1) |

EXAMPLE 3

A fabric of polyester fibres is padded with an aqueous preparation which contains, per liter, 1 g of a commercial dispersing agent based on fatty alcohol polyglycol ethers, 1 g of a commercial wetting agent based on alkyl-naphthalene-sulphonic acids, 4 g alginate thickening and a solution of 1 g of one of the compounds mentioned in Example 1(a) or 2(a) to (k) in 20 g triethanol amines. The fabric is then squeezed out to a weight increase of 100%, then dried, thermosolated at 190° for 1 minute and subsequently washed hot. Compared with the untreated fabric, the fabric thus treated shows a strong brilliant brightening effect of excellent fastness to light.

In comparison with the 3-phenyl-7-[3'-methyl- or 5'-phenyl-pyrazolyl-(1')]-coumarins described in Examples 3 and 6 of U.S. Pat. No. 3,123,617 the nearest comparable compounds according to the invention [Examples 1(a) and 2(f)] are distinguished by a stronger and more brilliant brightening effects.

The compounds mentioned in Example 2 under (a) and (g) are likewise substantially superior to the nearest comparable phenylpyrazolyl-coumarin described in Example 5 of the aforementioned U.S. Patent with regard to the brightening effect; furthermore, the compound 2(e) substantially surpasses the isomeric diphenylpyrazole compound mentioned in Example 8 of the U.S. Pat. with regard to the brightening effect.

EXAMPLE 4

6 kg terephthalic acid dimethyl ester and 5 liters ethylene glycol are mixed in an autoclave provided with stirrer with 0.05% zinc acetate and 0.03% (referred to the terephthalic acid methyl ester) of one of the compounds of the formula (I) described in Examples 1 and 2. The autoclave is heated to 180°, while stirring, trans-esterification starting at about 150°. The eliminated methanol is distilled off. The temperature is raised to 200° after 1 hour and to 220° after a further 45 minutes. The trans-esterification is then completed. The product thus obtained is pressed under nitrogen into an autoclave heated to 275° for pre-condensation. During pre-condensation the excess of glycol is distilled off. After 45 minutes a low vacuum is first applied which is increased to below 1 mm Hg in the course of a further 45 minutes. After about 2 hours 30 minutes the polycondensation is completed and the resultant melt is spun to filaments of final 50/25 denier. The filaments obtained exhibit an excellent brightening effect with high fastness to light and wet processing which are superior to the brightening effects attained with comparable compounds of U.S. Pat. No. 3.123,617.

EXAMPLE 5

A fabric obtained from polyester fibres is introduced, at a goods-to-liquor ratio 1:40, into a bath which contains, per liter, 1.5 g sodium oleyl sulphonate, 0.75 g formic acid, 2 g sodium chloride and 0.1 g of the compound described in Example 2 (k) in a dispersed form. The bath is heated to boiling within 30 minutes and kept at boiling temperature for 1 hour, the fabric being mechanically moved. The fabric is finally rinsed and dried. It then has an outstanding brightening effect.

EXAMPLE 6

1 g of the compound described in Example 2(h) or (i) is incorporated on the roll into 1 kg of an opaque soft polyvinyl chloride. The material is then outstandingly brightened and exhibits a brilliant and neutral white tint.

EXAMPLE 7

100 g polypropylene granulate and 1 g titanium dioxide (rutile) are intimately mixed at 210°–215° in a screw kneader and extruded over a slot die to give thin foils. A white film is formed. When 0.1 g of one of the compounds mentioned in Example 2 (c), (d), (h), (i) and (k) are added to the polypropylene granulate simultaneously with the titanium dioxide and the process is carried out in the manner indicated, then an outstandingly brightened foil is obtained with a fine clear white tint of good light fastness.

We claim:
1. A compound of the formula

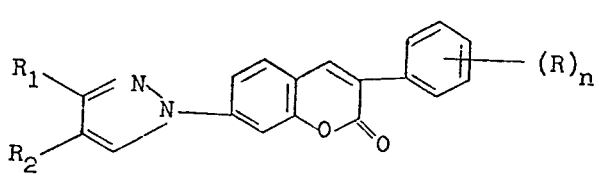

in which
R is H, F, Cl, Br, alkyl of 1–4 carbon atoms or alkoxy of 1–4 carbon atoms;
n is an integer of 1 to 3;
$R_1$ and $R_2$ are independently, alkyl or cycloalkyl of up to 8 carbon atoms; alkyl of up to 8 carbon atoms substituted with phenyl, tolyl or chlorophenyl; phenyl; phenyl substituted with F, Cl, Br, alkyl of 1–4 carbon atoms or alkoxy of 1–4 carbon atoms;
with the proviso that at least one of $R_1$ and $R_2$ is phenyl or the above substituted phenyl.

2. The compound of claim 1 in which $R_1$ is methyl; $R_2$ is phenyl;
R is hydrogen; and
n is 1.

3. A compound of the formula

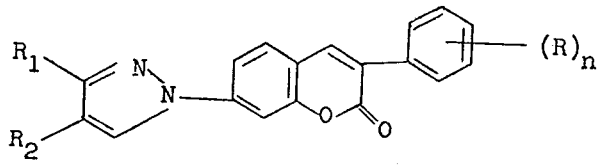

in which
R is H, F, Cl, Br, alkyl of 1–4 carbon atoms or alkoxy of 1–4 carbon atoms;
n is an integer of 1 to 3;
$R_1$ and $R_2$ independently, are phenyl; phenyl substituted with F, Cl, Br, alkyl having 1–4 carbon atoms or alkoxy having 1–4 carbon atoms; or alkyl of 1–8 carbon atoms substituted with phenyl, tolyl or chlorophenyl.

4. The compound of claim 3 in which $R_1$ is phenyl; $R_2$ is phenyl;
R is hydrogen; and
n is 1.

* * * * *